(12) United States Patent
Watanabe et al.

(10) Patent No.: US 6,299,840 B1
(45) Date of Patent: Oct. 9, 2001

(54) AUTOMATIC TESTING APPARATUS

(75) Inventors: Eiji Watanabe, Chikushino; Kanji Yahiro, Onojo; Akira Higuchi, Kasuga; Naoki Miyazaki, Karatsu; Kenichi Kuroda, Fukuoka; Kenji Ishiyama, Fukuoka; Takashi Daikoku, Fukuoka; Hideyoshi Kitahara, Kasuga, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/281,223

(22) Filed: Mar. 30, 1999

(30) Foreign Application Priority Data

Apr. 2, 1998 (JP) .................................. 10-089934

(51) Int. Cl.[7] .................................. G01N 21/00
(52) U.S. Cl. .......................... 422/63; 422/50; 422/68.1; 422/81
(58) Field of Search ............... 436/43–49; 422/50, 422/62–67, 55, 68.1, 81, 82.01, 129

(56) References Cited

U.S. PATENT DOCUMENTS

| | | | | |
|---|---|---|---|---|
| 4,298,570 | * | 11/1981 | Lillig et al. | 422/64 |
| 4,483,927 | * | 11/1984 | Takekawa | 436/43 |
| 4,554,839 | * | 11/1985 | Hewett et al. | 73/864.16 |
| 4,647,432 | * | 3/1987 | Wakatake | 422/64 |
| 5,055,408 | * | 10/1991 | Higo et al. | 436/48 |
| 5,332,549 | * | 7/1994 | MacIndoe | 422/63 |
| 5,356,525 | * | 10/1994 | Goodale | 204/299 R |

* cited by examiner

Primary Examiner—Jill Warden
Assistant Examiner—Yelena G. Gakh
(74) Attorney, Agent, or Firm—Stevens, Davis, Miller & Mosher, LLP

(57) ABSTRACT

In an automatic testing apparatus comprising, a specimen holder area adapted to hold thereon a specimen substrate for receiving therein a specimen, a reagent injector adapted to inject a reagent toward the specimen in the specimen substrate on the specimen holder area to mix the specimen with the reagent, a mixture reaction device adapted to hold thereon the specimen substrate including the mixture of the specimen and the reagent within a predetermined circumferential condition during a time period, and a transferring device for transferring the specimen substrate relative to the specimen holder area, the mixture reaction device has a take-in area to which the specimen substrate is transferred from the specimen holder area by the transferring device, and the take-in area is arranged adjacent to the specimen holder area.

25 Claims, 8 Drawing Sheets

AUTOMATIC TESTING APPARATUS

BACKGROUND OF THE INVENTION AND RELATED ART STATEMENT

The present invention relates to an automatic testing apparatus in which a specimen is mixed with a reagent and is subsequently stored to perform a reaction between the specimen and the reagent.

In the prior art, a transferring robot transfers a specimen receiving container between a specimen-reagent mixing device and a reaction performing device.

OBJECT AND SUMMARY OF THE INVENTION

An object of the present invention is to provide a high automatic-operating-efficiency and high testing-accuracy in an automatic testing apparatus in which a specimen is mixed with a reagent and is subsequently stored to perform a reaction between the specimen and the reagent.

According to the present invention, an automatic testing apparatus comprises, a specimen holder area adapted to hold thereon a specimen substrate or test plate for receiving therein a specimen, a reagent injector adapted to inject a reagent toward the specimen in the specimen substrate on the specimen holder area to mix the specimen with the reagent, a mixture reaction device adapted to hold thereon the specimen substrate including the mixture of the specimen and the reagent within a predetermined circumferential (environment) condition, for example, within a controlled temperature suitable for a reaction between the specimen and the reagent during a time period for performing sufficiently the reaction therebetween, and a transferring device for transferring the specimen substrate relative to the specimen holder area, wherein the mixture reaction device has a take-in area to which the specimen substrate is transferred from the specimen holder area by the transferring device, and the take-in area is arranged adjacent to the specimen holder area.

Since the take-in area to which the specimen substrate is transferred from the specimen holder area by the transferring device is arranged adjacent to the specimen holder area, a time necessary for transferring the specimen substrate by the transferring device between the mixing between the specimen and the reagent and the reaction therebetween within the predetermined circumferential ential condition, that is, an undesirable time loss causing an undesirable reaction proceeding within an undesirable circumferential condition different from the predetermined termined circumferential condition after the mixing, is minimized. Therefore, the operating-efficiency and testing-accuracy in the automatic testing apparatus is improved.

If the automatic testing apparatus comprises a specimen substrate stocking device adapted to hold thereon the specimen substrate before mixing the specimen with the reagent on the specimen holder area, the specimen substrate stocking device has a take-out area from which the specimen substrate is transferred to the specimen holder area by the transferring device, and the take-out area is arranged adjacent to the specimen holder area, a transferring movement of the transferring device is performed around the specimen holder area as a central point of the transferring movement of the specimen substrate so that a time within which the transferring device returns to the specimen holder area from the specimen substrate stocking device is minimized. Therefore, the undesirable time loss causing the undesirable reaction proceeding within the undesirable circumferential condition different from the predetermined circumferential condition after the mixing between the specimen and the reagent and the transferring of the specimen substrate relative to the specimen substrate stocking device is minimized to improve the operating-efficiency and testing-accuracy in the automatic testing apparatus. The specimen holder area may be arranged between the take-in area and the take-out area in a transferring direction of the transferring device and/or in a proceeding direction of the specimen substrate so that the specimen substrate is prevented from proceeding between the take-in area and the specimen holder area over or through the take-out area and from proceeding between the take-out area and the specimen holder area over or through the take-in area. If the take-in area and the take-out area face to each other through the specimen holder area, the specimen substrate transferring direction of the transferring device may be simplified or as straight as possible.

When the specimen holder area is adapted to hold thereon a plurality of the specimen substrates, and the transferring device transfers one of the specimen substrates over another one of the specimen substrates, a horizontal area in which the transferring device moves can be small so that a horizontal size of the automatic testing apparatus can be small.

When the automatic testing apparatus comprises a mixture testing device for measuring a condition (for example, chemical and/or biochemical characteristic, physical characteristic or the like) of the mixture of the specimen and the reagent on the specimen substrate, and the transferring device transfers the specimen substrate from the specimen holder area on which the mixture is formed to the mixture testing device arranged at a relatively lower position in comparison with a vertical position of the specimen holder area, the mixing degree of the mixture is increased by the vertical movement of the specimen substrate.

DETAILED DESCRIPTION OF PREFERRED EMBODIMENTS

Figure 1:
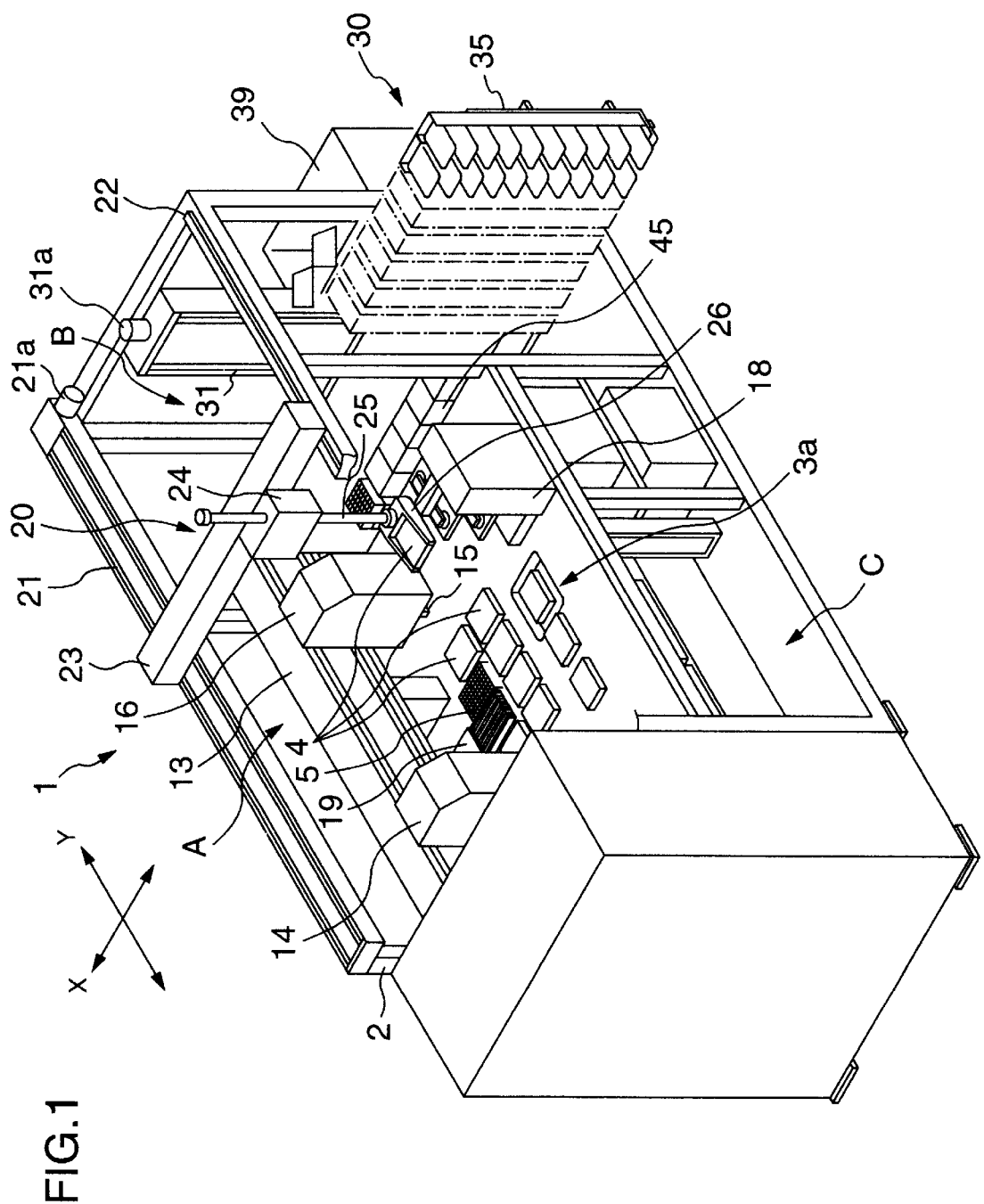
FIG. 1 is an oblique projection view showing an automatic testing apparatus of the invention.

As shown in FIG. 1, an automatic testing or screening test apparatus 1 includes a frame 2 composed of structural angles and a base plate 3 as a main body thereof. The apparatus 1 is divided by the frame 2 and the base plate 3 into a mixing section A, a stock section B, a treatment section C and a reaction section D. The mixing section A is formed on the base plate 3 to mix a reagent with a specimen in a specimen substrate 4. A plurality of the specimen substrates containing the specimens and injection tips are stocked in the stock section B. The reaction section D contains a mixture of the specimen and the reagent on the specimen substrate during a time period as an incubator while keeping them in a desirable circumferential condition. The treatment section C receives the specimen substrate from the reaction section D to measure or analyze a condition of the mixture and/or clean the specimen substrate after the reaction in the reaction section D between the specimen and the reagent.

Figure 2:
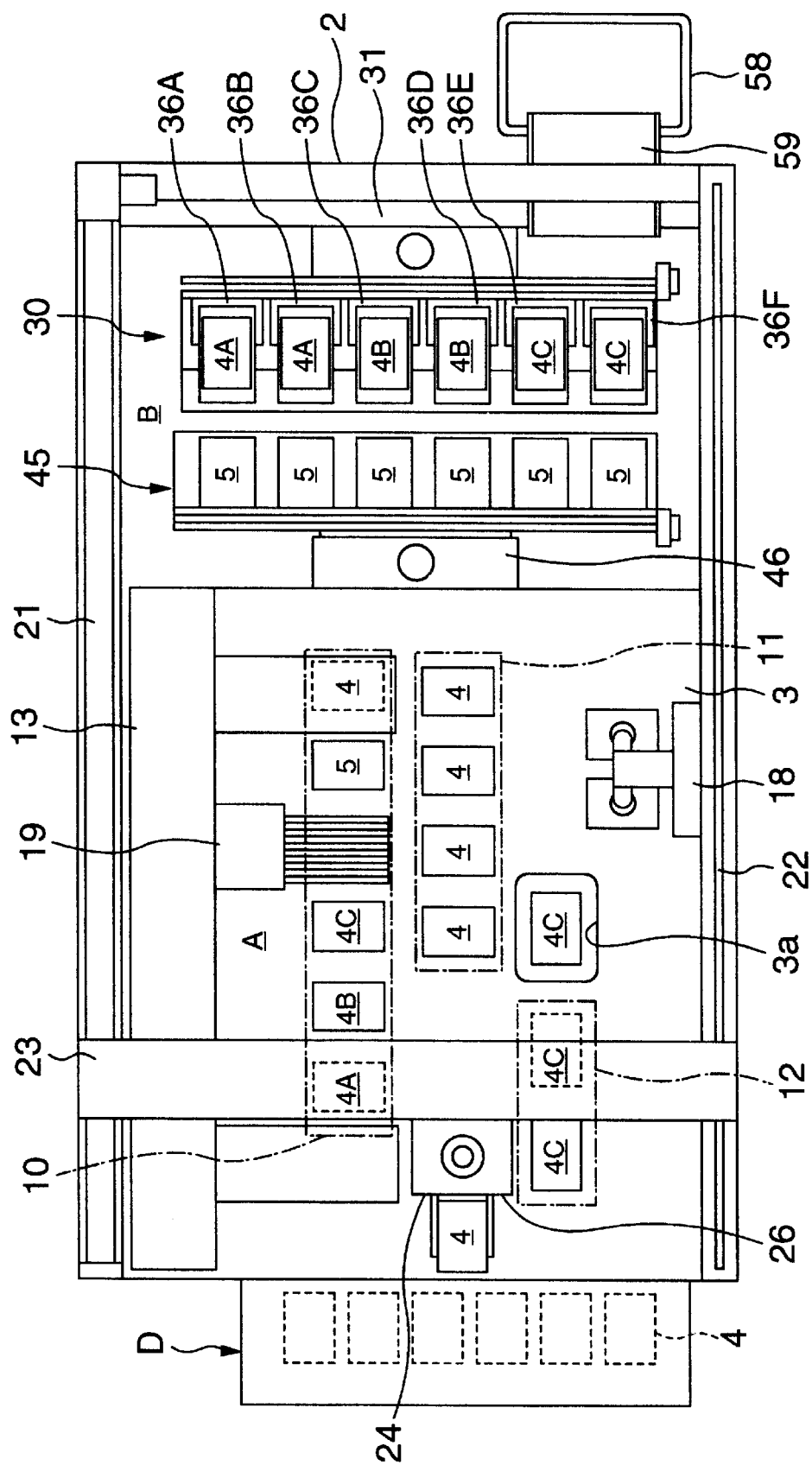
FIG. 2 is a front view of the automatic testing apparatus of the invention as seen from a view point vertically higher than the apparatus.

As shown in FIG. 2, the mixing section A includes a specimen holder area 10 as the claimed specimen holder area, a specimen buffer area 11 and a waiting specimen area 12 on the base plate 3. On the specimen holder area 10, the specimen in the specimen substrate 4 is mixed with the reagent. The specimen buffer area 11 (which may be included by the claimed specimen holder area) holds temporarily the specimen substrate 4 before transferred to the specimen holder area 10. The waiting specimen area 12 (which may be included by the claimed specimen holder area) holds temporarily the specimen substrate 4 before transferred through a transfer hole 3a of the base plate 3 to the treatment section C below the mixing section A. The mixing section A further includes a reagent injector formed by a slide table 13 extending in a longitudinal direction of the specimen holder area 10, and first and second injection heads 14 and 16 moved horizontally along the slide table 13 and vertically over the specimen holder area 10 as a common operating area of the first and second injection heads 14 and 16 so that both of the first and second injection heads 14 and 16 inject the reagent to the specimen in the specimen substrate on the specimen holder area 10.

Figure 4:
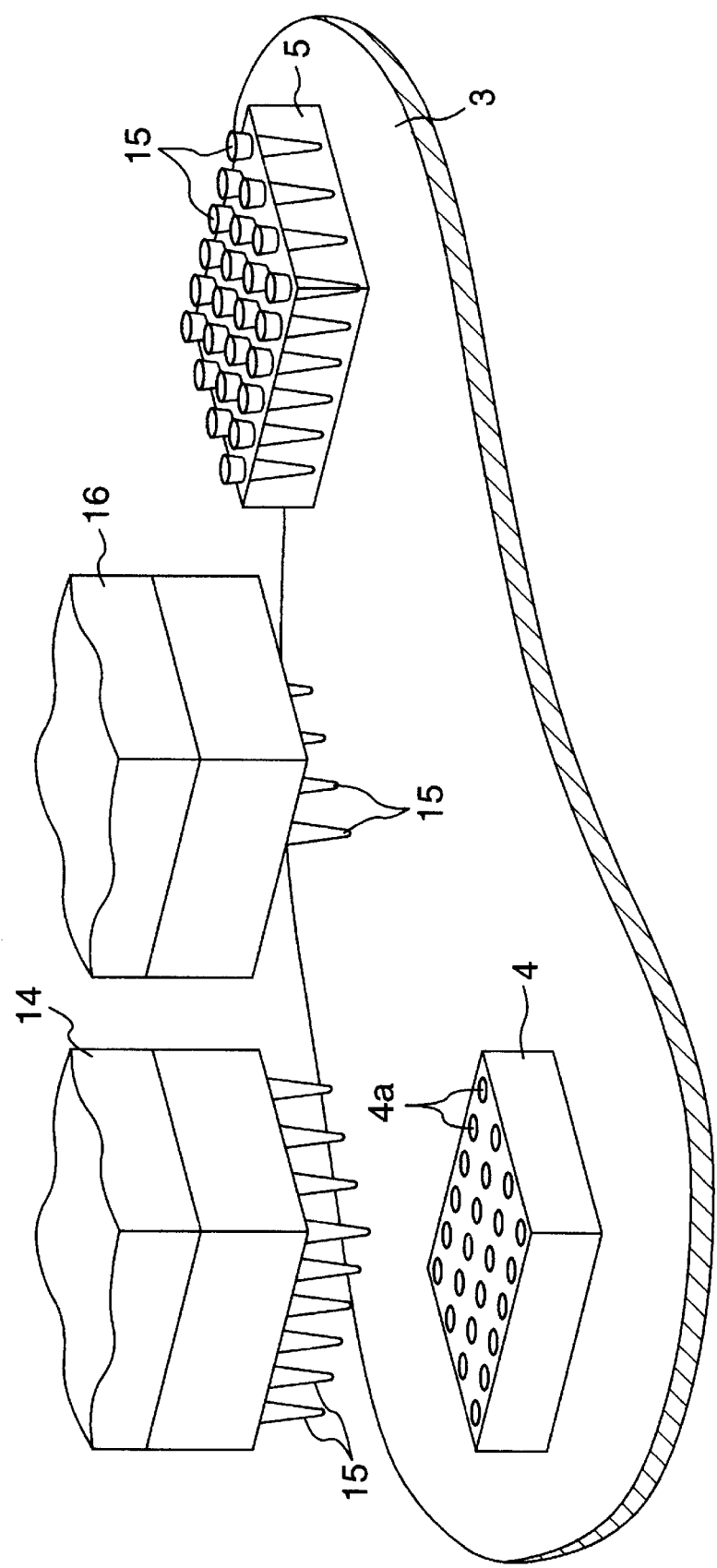
FIG. 4 is an oblique projection view showing a reagent injector of the automatic testing apparatus of the invention.
Figure 6:
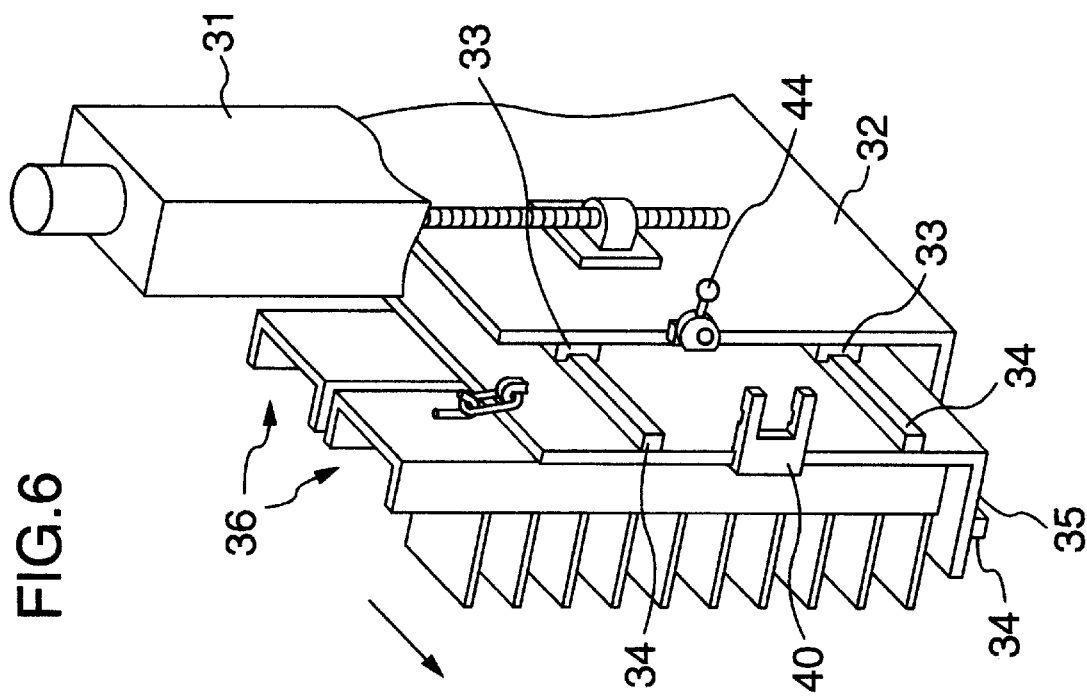
FIG. 6 is an oblique projection view showing the specimen substrate stocking device on a removal position thereof.

As shown in FIG. 4, each of the first and second injection heads 14 and 16 holds at least one exchangeable tip 15 through which the reagent is injected to the specimen to be mixed therewith, the specimen is sucked and injected to another specimen, and/or the mixture of the specimen and the reagent is sucked and injected to the another specimen, another mixture of the specimen and the reagent or the like. The exchangeable tip 15 is contained in a tip container 5 and is attached therefrom to the first and second injection heads 14 and 16 by the vertically downward movement of the injection heads 14 and 16. A tip remover mechanism 19 as shown in FIGS. 1 and 2 has on the mixing section A, a comb-teeth shaped plate which is engaged with the tip 15 by displacement of the injection head 14 and/or 16 so that the tip 15 is removed from the injection head 14 and/or 16 by the vertically upward movement of the injection head 14 and/or 16. A cover for covering the specimen substrate 4 is removed by a cover remover unit 18 arranged on the base plate 3 at an opposite side of the slide table 13.

Figure 3:
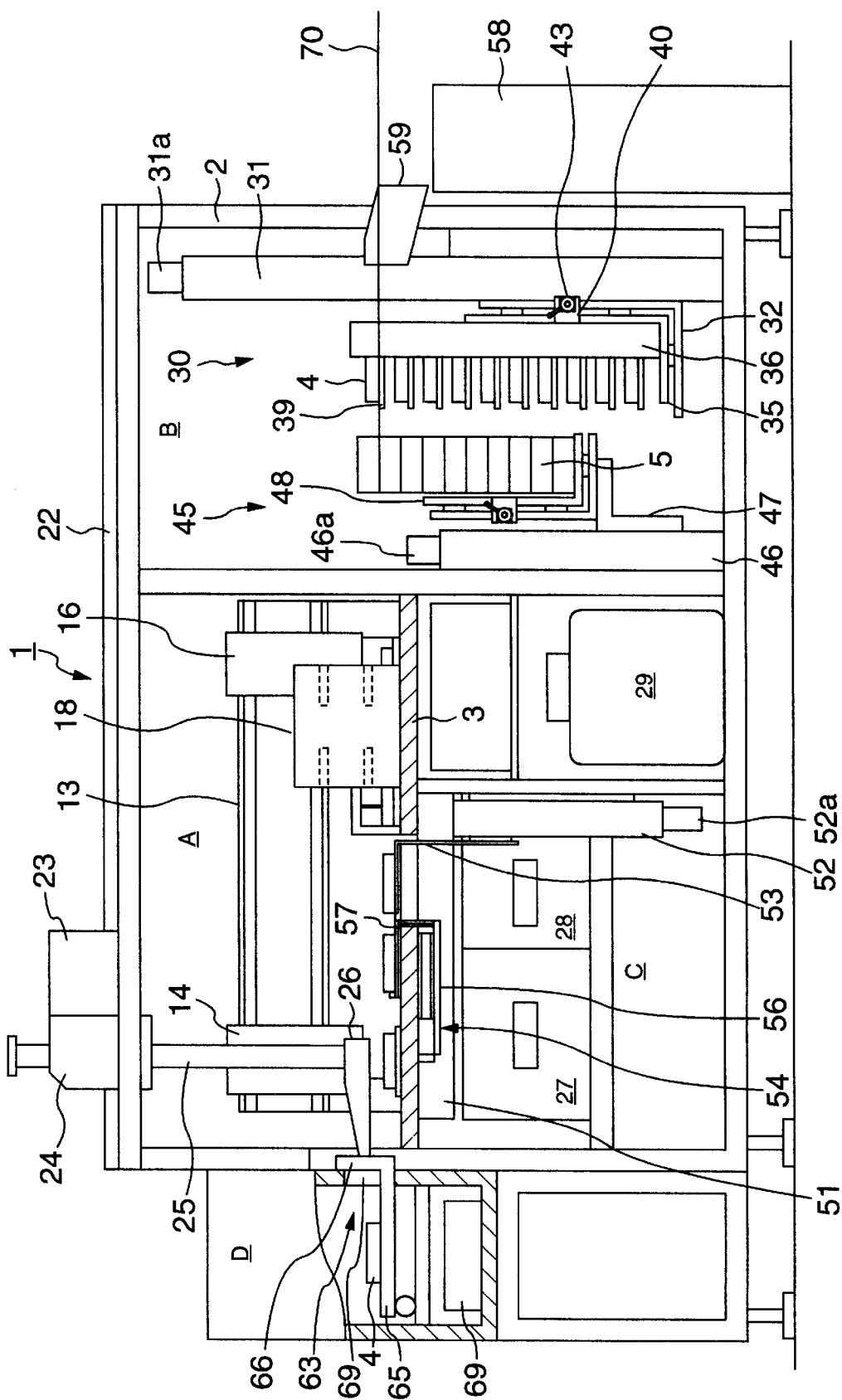
FIG. 3 is a side view of the automatic testing apparatus of the invention.
Figure 5:
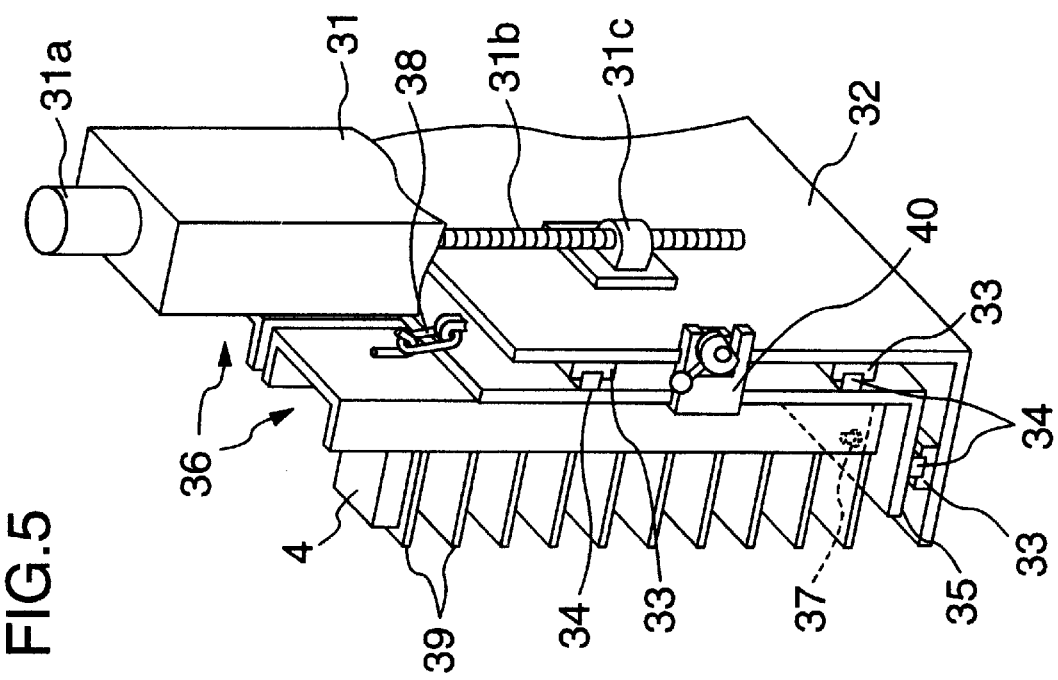
FIG. 5 is an oblique projection view showing a specimen substrate stocking device of the automatic testing apparatus of the invention on a normal position thereof.

As shown in FIGS. 2 and 3, the stock section B has at least one substrate stocking device 30 and at least one tip stocking device 45. The substrate stocking device 30 is vertically movably guided by a Z-axis table 31, and a container part of the substrate stocking device 30 is movably guided by a slide mechanism (described below) so that the container part may be shifted to an outside of the stock section B. As shown in FIG. 5, the Z-axis table 31 has a Z axis-motor 31a for rotationally driving a feed screw 31b which engages within a nut 31c fixed to an L-shaped back plate 32. The back plate 32 has three slide guides 33 one of which is arranged at a bottom portion of the back plate 32 and the other two of which are juxtaposed vertically at an upright portion thereof. The slide guides 33 are movably fitted in respective horizontally extending guide rails 34 on an L-shaped magazine holder 35. A plurality of magazines 36 are detachably mounted on the magazine holder 35. The magazines 36 are positioned by pins 37 relative to the magazine holder 35 and fixed to the magazine holder 35 by locks 38. The magazine holder 35, the pins 37 and the locks 38 form a magazine mounting device. Each of the magazines 36 has racks 39 each of which receives thereon the specimen substrate 4.

As shown in FIG. 2, the magazines 36A and 36B hold thereon the, specimen substrates 4A including a dilution liquid, the magazines 36C and 36D hold thereon the specimen substrates 4B including a reagent, and the magazines 36E and 36F hold thereon the specimen substrates 4c including the specimen. By energizing the Z axis-motor 31a, a desirable one of the specimen substrates 4 on the magazines 36 is positioned vertically to a suitable height 70 for being clamped by a transfer head (described below). The desirable one of the specimen substrates 4 on the magazines 36 on the suitable height is deemed to be at the claimed take-out area.

A combination of the vertical movements of the magazines 36 and the transfer head enable the magazines 36 to include large number of the racks 39 in a limited vertical length. The magazine holder 35 can slide horizontally on a slide mechanism of the guide rails 34 and the slide guides 33 to an outside of the stock section B so that the magazines 36 or the specimen substrates 4 can be easily exchanged. At least one of the magazines 36 may be prepared at the outside of the stock section B while another one of the magazines 36 is set in the stock section B, and may be set into the stock section B just after the another one of the magazines 36 becomes unnecessary.

Figure 7:
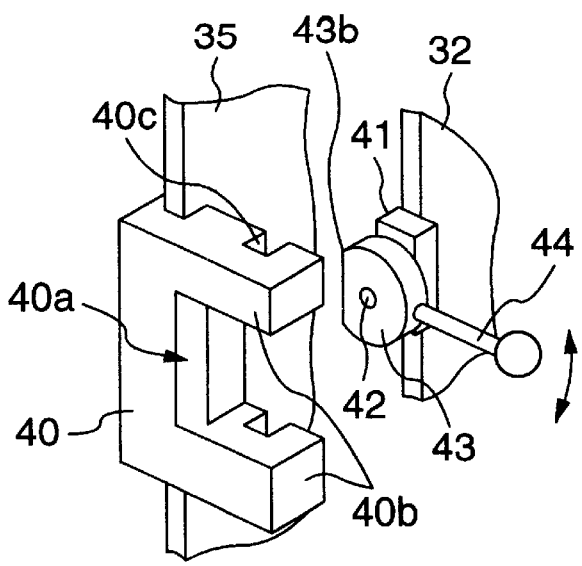
FIG. 7 is an oblique projection view showing a magazine holder.
Figure 8:
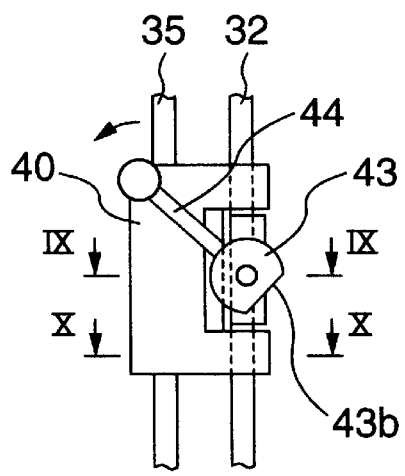
FIG. 8 is a side view of the magazine holder.
Figure 9:
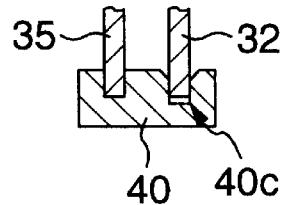
FIG. 9 is a cross sectional view taken along a line IX—IX of FIG. 8.
Figure 10:
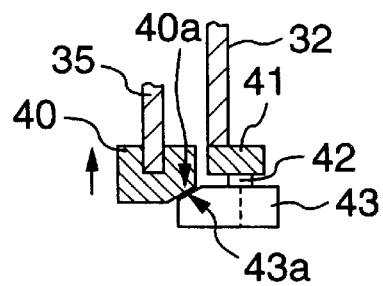
FIG. 10 is a cross sectional view taken along a line X—X of FIG. 8.

As shown in FIGS. 5–10, a U-shaped fixing member 40 is attached to an end of the magazine holder 35 to fix the magazine holder 35 to the back plate 32. The fixing member 40 has a vertically extending tapered surface 40a (as shown in FIG. 9) and vertically extending slots 40c in projections 40b. A bracket 41 is attached to an end of the back plate 32, and a substantially cylindrical rotatable member 43 is fitted in a pin 42 projecting from the bracket 41. The rotatable member 43 has a lever 44 to be rotated thereby on the pin 42, and a flat surface 43b to prevent an interference relative to the fixing member 40. As shown in FIG. 7, when the flat surface 43b is kept to extend in a vertical direction, the magazine holder 35 is set onto the back plate 32.

As shown in FIG. 8, the rotatable member 43 is arranged between the projections 40b of the fixing member 40 when the magazine holder 35 is pushed onto the back plate 32, and subsequently a tapered surface 43a of the rotatable member 43 contacts the tapered surface 40a of the fixing member 40 to push the magazine holder 35 in a direction denoted by an arrow shown in FIG. 9 and the end of the magazine holder 35 contacts the slots 40c so that the magazine holder 35 is fixed horizontally to the back plate 32 when the lever 44 is rotated in a direction denoted by an arrow shown in FIG. 8.

The tip stocking device 45 is opposed to the substrate stocking device 30 in the stock section B, and includes a up-and-down table 47 driven by a motor 46a along a Z-axis table 46. A movable plate 48 with a slide mechanism similar to that of the substrate stocking device 30 is mounted on the up-and-down table 47, and receives a plurality of the tip containers 5 in a stacking manner. Any one of the tip containers 5 is positioned along the Z-axis table 46 to the suitable height 70 for being clamped by the transfer head (described below).

A first transfer device includes a Y-axis table 21, an X-axis table 23, an up-and-down and rotational unit 24 and a transfer head 26. The Y-axis table 21 extends in a longitudinal direction of the apparatus on an end of the frame 2, and the X-axis table 23 is movable at an end thereof along the Y-axis table 21 and at another end thereof along a guide rail 22 on the frame 2, in a Y direction. The up-and-down and rotational unit 24 is movable along the X-axis table 23 in an X direction. The transfer head 26 is mounted on a lower end of an arm 25 projecting downward from the up-and-down and rotational unit 24. The specimen substrate 4 or the tip container 5 is held between clamping members 26a of the transfer head 26, so that the first transfer device clamps and transfers the plates 4 prepared on the racks 39 of the substrate stocking device 30 and the tip containers 5 prepared on the movable plate 48 of the magazine holder 35 between the mixing section A and the stock section B and between the mixing section A and the reaction section D.

As shown in FIG. 3, in the treatment section C, an analyzer 27 for measuring a condition of the mixture in the specimen substrate 4 and a cleaner 28 for cleaning the specimen substrate 4 with removal of the specimen or the mixture are arranged below the base plate 3. A waste liquid tank 29 into which a waste liquid used in the cleaner 28 to clean the specimen substrate 4 is fed is arranged at a side of the cleaner 28.

Figure 11:
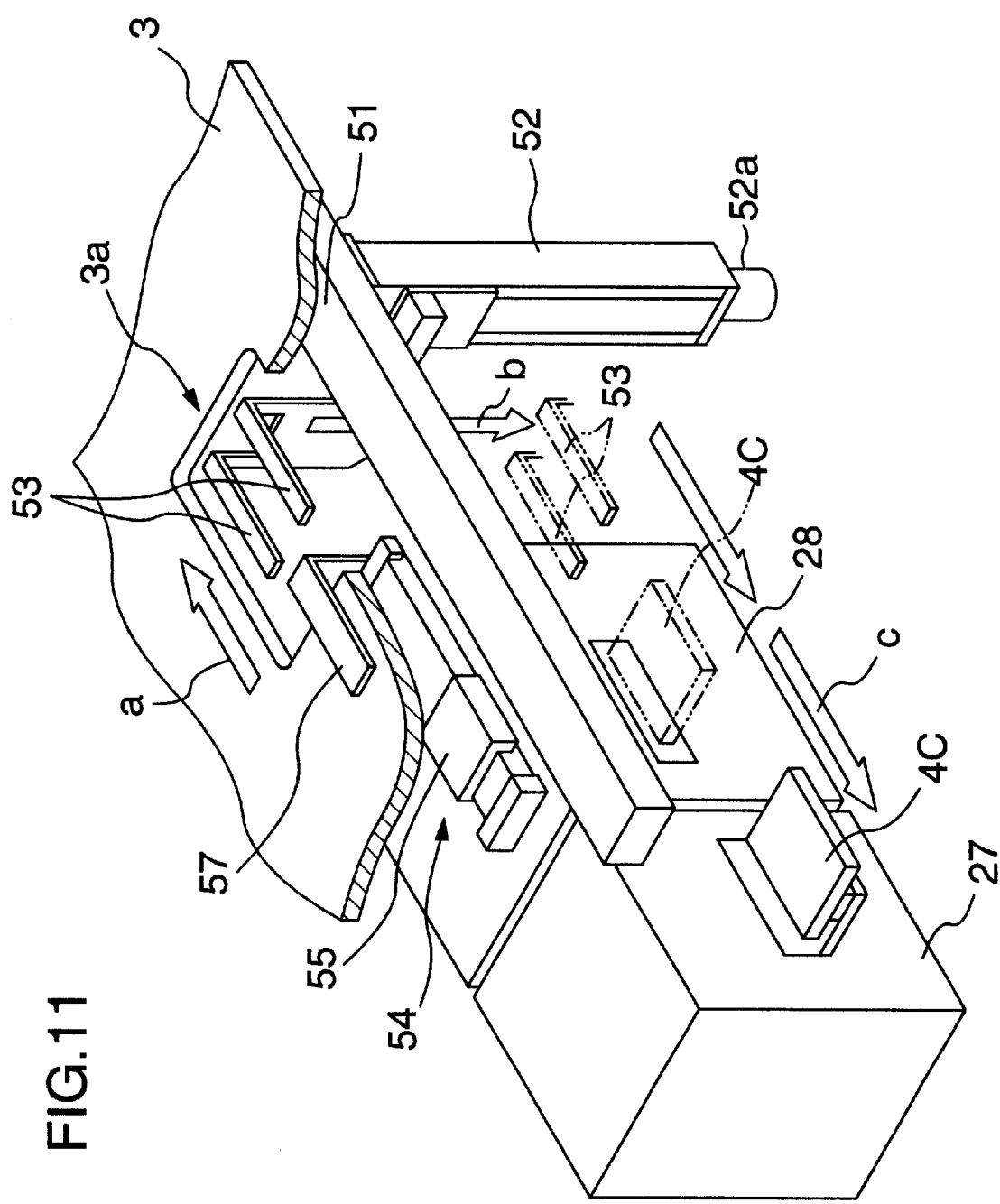
FIG. 11 is an oblique projection view showing a transferring device between a specimen holder area and a mixture testing device.
Figure 12:
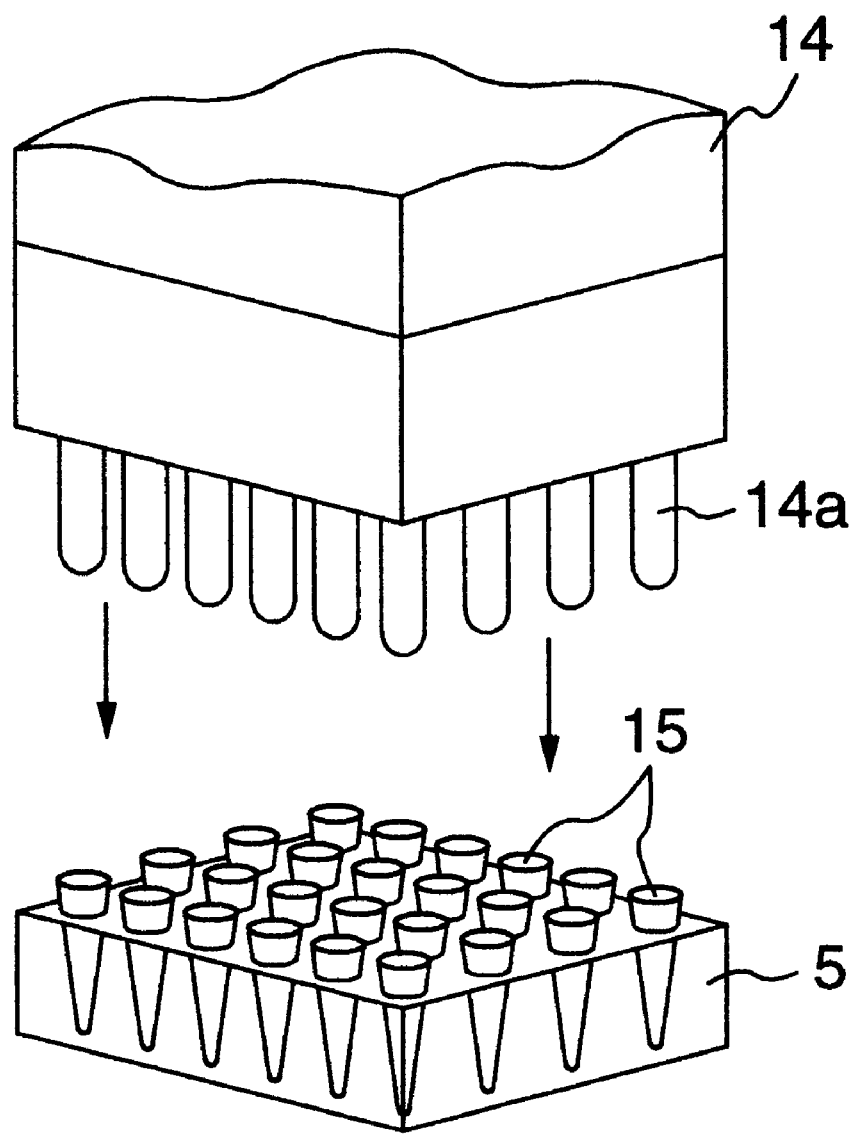
FIG. 12 is an oblique projection view showing a reagent injection head.

As shown in FIGS. 3 and 11, a second transfer device for transferring between the mixing section A and the treatment section C has a Y-axis table 51 at an out-side of the transfer hole 3a under the base plate 3, and a Z-axis table 52 movable horizontally along the Y-axis table 51. A vertical transfer arm 53 including two L-shaped nails is driven vertically by a motor 52a along the Z-axis table 52 to transfer the specimen substrate 4 to the analyzer 27 and/or the cleaner 28.

A slide unit 54 extends substantially parallel to the Y-axis table 51 under the base plate 3, and includes a movable slider 55 with a horizontal transfer arm 57 and a connection member 56. The transfer arm 57 extends through the transfer hole 3a over an upper surface of the base plate 3 to transfer the specimen substrate 4 from the mixing section A to a position over the transfer arm 53. Subsequently, the transfer arm 57 moves away from the position after the transfer arm 53 ascends relative to the transfer arm 57 to mount thereon the specimen substrate 4. The specimen substrate 4 on the transfer arm 53 is transferred to the analyzer 27 and/or the cleaner 28 by a vertical downward movement of the transfer arm 53 along the Z-axis table 52 and a horizontal movement thereof along the Y-axis table 51. A reverse operation of the above described operation may be performed to transfer the specimen substrate 4 from the analyzer 27 and/or the cleaner 28 to the mixing section A.

A waste box 58 is arranged at a side of the stock section B to receive through a waste guide 59 the specimen substrate 4 and/or the tip container 5 transferred by the transfer head 26 after being used.

As shown in FIG. 3, the reaction section D as the claimed mixture reaction device includes a container defined by an adiabatic wall 61 and a temperature and humidity adjuster 62 for an inside of the container. The container has an opening 63 as the claimed take-in area adjacent to the mixing section A. The specimen substrate 4 is set by the transfer head 26 from the mixing section A onto a movable rack 65 projecting from the container, and is received through the opening 63 into the container by pushing the rack 65 into the container. By pushing out the rack from the container, the specimen substrate 4 is transferred through the opening 63 from the reaction section D to the mixing section A. The rack 65 has a cover portion 66 to cover the opening 63 when the rack 65 is pushed into the container.

The tip container 5 is transferred by the transfer head 26 from the tip stocking device 45 onto a part of the specimen holder area 10. The injection head 14 and/or 16 descend in order onto the tip container 5 to attach the injection tip 15 to a pipette 14a of the injection head 14 and/or 16. The specimen substrates 4A including the dilution liquid, the specimen substrates 4B including the reagent, and the specimen substrates 4c including the specimen are set on the specimen holder area 10 from the substrate stocking device 30 by the transfer head 26. The injection head 14 and/or 16 descends to the specimen substrates 4A to suck in the dilution liquid, ascends and moves horizontally, and descends to the specimen substrates 4C to discharge the dilution liquid as the claimed reagent into the specimen in the specimen substrates 4C. Thereafter, the specimen substrate 4C is transferred by the transfer head 26 from the specimen holder area 10 through the opening 63 of the container to the reaction section D. The specimen substrates 4C is transferred by the transfer head 26 from the reaction section D through the opening 63 of the container to the specimen holder area 10 (if necessary through the specimen buffer area 11) after being received in the reaction section D for a desired time period sufficient for a reaction between the specimen and the dilution liquid. On the specimen holder area 10, the reagent for detecting a result of the reaction between the specimen and the dilution liquid is injected into the mixture of the specimen and the dilution liquid in the specimen substrate 4C from the injection head 14 and/or 16 which previously sucked in the reagent from the specimen substrate 4B. After temporarily held on the waiting specimen area 12, the specimen substrate 4C is transferred by the transfer head 26 onto the transfer arm 57 to be further transferred by the second transfer device to the analyzer 27 in the treatment section C. An analyzing result of the mixture of the specimen, the dilution liquid and the reagent by the analyzer 27 is recorded with a corresponding specimen-reference-code, mixing-process-reference-code, reaction-process-reference-code and so forth. Thereafter, the specimen substrate 4C may be transferred through the mixing section to the stock section B by the second transfer device and the transfer head 26 if a further mixing with the specimen, the dilution liquid and/or the reagent. Alternatively, the specimen substrate 4C may be transferred to the cleaner 28. The cleaned specimen substrate 4C may be stored on the magazine 36 or fed into the waste box 58.

What is claimed is:

1. An automatic testing apparatus for testing a specimen received in a test plate, said apparatus comprising:

a main body, said main body including a specimen holder for holding a test plate;

a reagent injector within the main body, for injecting a reagent onto the specimen received in the test plate to form a mixture;

a mixture reaction device for engaging the main body and for holding therein the test plate and mixture for a period of time sufficient for a reaction to occur between the specimen and the reagent, said reaction device having a take-in area comprising an opening through which the test plate and mixture is transferred into the reaction device, wherein the reaction device further has a cover for covering the take-in area when the test plate and mixture are transferred into the reaction device;

a transferring device within the main body, for transferring the test plate from at least the specimen holder area to at least the take-in area; and a mixture testing device for measuring a condition of the mixture of the specimen and the reagent on the test plate, wherein the transferring device transfers the test plate with the mixture from the specimen holder area to the mixture testing device, said testing device being arranged at a relatively lower position in comparison with a vertical position of the specimen holder area.

2. An automatic testing apparatus according to claim 1, further comprising a test plate stocking device for holding thereon the test plate before mixing the specimen with the reagent on the specimen holder area, wherein the test plate stocking device has a take-out area from which the test plate is transferred to the specimen holder area by the transferring device, wherein the take-out area is disposed adjacent to the specimen holder area.

3. An automatic testing apparatus according to claim 2, wherein the specimen holder area is arranged between the take-in area and the take-out area.

4. An automatic testing apparatus according to claim 2, wherein the take-in area and the take-out area face to each other through the specimen holder area.

5. An automatic testing apparatus according to claim 1, wherein a temperature of the mixture of the specimen and the reagent is kept at a predetermined degree in the mixture reaction device.

6. An automatic testing apparatus according to claim 1, wherein the reagent injector has an injection head including a tip through which the reagent is injected.

7. An automatic testing apparatus according to claim 2, wherein the test plate stocking device has a magazine for holding thereon a plurality of the test plates arranged along a vertical axis.

8. An automatic testing apparatus according to claim 7, wherein the magazine is movable vertically.

9. An automatic testing apparatus according to claim 7, wherein the magazine is detachable from the testing apparatus.

10. An automatic testing apparatus according to claim 7, wherein the magazine is movable horizontally to a removal position at which the magazine is detachable from the testing apparatus.

11. An automatic testing apparatus according to claim 1, wherein the transferring device has a holding head for holding the test plate, and the holding head is movable in horizontal directions perpendicular to each other and rotatable on a vertical axis.

12. An automatic testing apparatus for testing a specimen received in a test plate, comprising:

a main body;

said main body including a specimen holder area for holding a plurality of the test plates;

a reagent injector within the main body, for injecting a reagent onto the specimen received in the test plate to form a mixture;

a mixture reaction device that engages the main body, for holding therein the test plate and mixture for a period of time sufficient for a reaction to occur between the specimen and the reagent, said reaction device having a take-in area comprising an opening, adjacent to the specimen holding area, to which the test plate and mixture are transferred into the reaction device; and a transferring device within the main body, for transferring the test plate from at least the specimen holder area to at least the take-in area and also for transferring the test plate over another test plate held on the specimen holder area.

13. An automatic testing apparatus for testing a specimen received in a teat plate, said apparatus comprising:

a main body, said main body including a specimen holder area for holding a plurality of test plates;

a reagent injector within the main body, for injecting a reagent onto the specimen received in the test plate to form a mixture, wherein the reagent injector has a plurality of injection heads movable relative to each other over a common area on which the specimen holder area is arranged, and each of the injection heads includes a tip through which the reagent is injected;

a mixture reaction device that engages the main body, for holding therein the test plate and mixture for a period of time sufficient for a reaction to occur between the specimen and the reagent, said reaction device having a take-in area comprising an opening, adjacent to the specimen holding area, to which the test plate and mixture are transferred;

a transferring device within the main body, for transferring the test plate from the specimen holder area to the take-in area; and a mixture testing device for measuring a condition of the mixture of the specimen and the reagent on the test plate, wherein the transferring device transfers the test plate with the mixture from the specimen holder area to the mixture testing device, said testing device being arranged at a relatively lower position in comparison with a vertical position of the specimen holder area.

14. An automatic testing apparatus for testing a specimen received in a test plate, said apparatus comprising:

a main body;

a test plate stocking device that engages the main body, for holding the test plate, said stocking device having a take-out area from which the test plate is transferred;

a specimen holder area within the main body, for holding a test plate;

a reagent injector within the main body, for injecting a reagent onto the specimen received in the test plate to form a mixture;

a mixture reaction device that engages the main body, for holding therein the test plate and mixture for a period of time sufficient for a reaction to occur between the specimen and the reagent said reaction device having a take-in area through which the test plate is transferred into the reaction device;

a mixture testing device within the main body, for measuring a condition of the mixture, wherein the position of the testing device is vertically lower than the position of the specimen holder area;

a transferring device within the main body, for transferring the test plate from the take-out area to the specimen holder area and from the specimen holder area to the take-in area, wherein the take-out area and the take-in area a re each adjacent to the specimen holder area on substantially opposite sides of the specimen holder such that the take-in are a and the take-out area face each other along a horizontal axis through the specimen holder a area; and a mixture testing device for measuring a condition of the mixture of the specimen and the reagent an the test plate, wherein the transferring device transfers the test plate with the mixture from the specimen holder area to the mixture testing device, said testing device being arranged at a relatively lower position in comparison with a vertical position of the specimen holder area.

15. An automatic testing apparatus according to claim 14, wherein the specimen holder area is arranged between the take-in area and the take-out area.

16. An automatic testing apparatus according to claim 14, wherein a temperature of the mixture of the specimen and the reagent is kept at a predetermined degree in the mixture reaction device.

17. An automatic testing apparatus according to claim 14, wherein the reagent injector has an injection head including a tip through which the reagent is injected.

18. An automatic testing apparatus for testing a specimen received in a test plate, comprising:

a main body;

said main body including a specimen holder area for holding a plurality of test plates;

a reagent injector within the main body, for injecting a reagent onto the specimen received in the test plate to form a mixture;

a mixture testing device within the main body, for measuring a condition of the mixture, wherein the position of the testing device is vertically lower than the position of the specimen holder area; and a transferring device within the main body, for transferring the test plate to and from the specimen holder area and also for transferring said test plate over another test plate held in the specimen holder area.

19. An automatic testing apparatus for testing a specimen received in a test plate, said apparatus comprising:

a main body, said main body including a specimen holder area for holding a test plate;

a reagent injector within the main body, for injecting a reagent onto the specimen received in the test plate to form a mixture, wherein the reagent injector has a plurality of injection heads movable relative to each other over a common area on which the specimen holder area is arranged, and each of the injection heads includes a tip through which the reagent is injected;

a mixture testing device within the main body, for measuring a condition of the mixture, wherein the position of the testing device is vertically lower than the position of the specimen holder area;

a transferring device within the main body, for transferring the test plate to and from the specimen holder area; and a mixture testing device for measuring a condition of the mixture of the specimen and the reagent an the test plate, wherein the transferring device transfers the test plate with the mixture from the specimen holder area to the mixture testing device, said testing device being arranged at a relatively lower position in comparison with a vertical position of the specimen holder area.

20. An automatic testing apparatus according to claim 19, further comprising a tip remover on the common area to remove the tip from the injection head.

21. An automatic testing apparatus according to claim 14, wherein the test plate stocking device has a magazine for holding thereon a plurality of the test plates arranged along a vertical axis.

22. An automatic testing apparatus according to claim 21, wherein the magazine is movable vertically.

23. An automatic testing apparatus according to claim 21, wherein the magazine is detachable from the testing apparatus.

24. An automatic testing apparatus according to claim 21, wherein the magazine is movable horizontally to a removal position at which the magazine is detachable from the testing apparatus.

25. An automatic testing apparatus according to claim 14, wherein the transferring device has a holding head for holding the test plate, and the holding head is movable in horizontal directions perpendicular to each other and rotatable on a vertical axis.

* * * * *